United States Patent [19]
Nugteren et al.

[11] Patent Number: 5,629,201
[45] Date of Patent: May 13, 1997

[54] APPARATUS FOR APPLYING A LIQUID SAMPLE ONTO A CULTURE MEDIUM

[75] Inventors: Robert J. Nugteren, Nieuw Vennep; Arie H. Rodenburgh, Hoofddorp; Erik A. Aurik, Haarlem, all of Netherlands

[73] Assignee: Priolion Development B.V., Vijfhuizen, Netherlands

[21] Appl. No.: 343,425

[22] PCT Filed: May 24, 1993

[86] PCT No.: PCT/NL93/00110

§ 371 Date: Feb. 9, 1995

§ 102(e) Date: Feb. 9, 1995

[87] PCT Pub. No.: WO93/24609

PCT Pub. Date: Dec. 9, 1993

[30] Foreign Application Priority Data

May 22, 1992 [NL] Netherlands .................. 9200909

[51] Int. Cl.⁶ .................................................. C12M 1/26
[52] U.S. Cl. ........................ 435/283.1; 435/286.4; 435/309.1; 422/100
[58] Field of Search .................... 435/30, 286.3, 435/286.4, 286.5, 309.1, 309.4, 283.1; 422/100; 436/49; 73/869.16, 864.87; 222/567, 74, 527; 118/256, 323; 346/131, 139 R, 139 C, 140.1; 239/397, 442, 600

[56] References Cited

U.S. PATENT DOCUMENTS

| | | |
|---|---|---|
| 2,223,254 | 11/1940 | Hite ........................... 118/256 |
| 3,484,206 | 12/1969 | Loebl ......................... 422/100 |
| 3,547,781 | 12/1970 | Guigan et al. ............... 195/127 |
| 3,731,648 | 5/1973 | Gerber et al. ............. 346/139 R |
| 3,778,351 | 12/1973 | Rosov ....................... 435/309.1 |
| 3,841,973 | 10/1974 | Wilkins et al. ............. 195/127 |
| 3,884,765 | 5/1975 | Wilkins et al. ............. 195/127 |
| 3,892,632 | 7/1975 | Campbell et al. .......... 435/309.1 |
| 4,273,877 | 6/1981 | Anagnostopoulos ......... 435/309.1 |
| 4,785,629 | 11/1988 | Ennis et al. ................... 60/584 |
| 4,823,148 | 4/1989 | Sieber et al. ............. 346/139 R |
| 5,101,219 | 3/1992 | Gerber et al. ............. 346/139 R |
| 5,213,761 | 5/1993 | Sakagami ...................... 436/49 |
| 5,384,093 | 1/1995 | Ootani et al. ................. 436/49 |

FOREIGN PATENT DOCUMENTS

| | | |
|---|---|---|
| 2809032 | 9/1978 | Germany. |
| 2829921 | 1/1980 | Germany ..................... 346/140.1 |
| 3-041364 | 2/1991 | Japan ......................... 435/286.4 |
| 7207375 | 12/1972 | Netherlands. |
| 2025457 | 1/1980 | United Kingdom. |

*Primary Examiner*—William H. Beisner
*Attorney, Agent, or Firm*—Kinney & Lange, P.A.

[57] ABSTRACT

An apparatus for applying a liquid sample onto a culture medium in a spiral shape, for example, for determining the bacteria concentration therein, having a line that has an incline nozzle for applying the liquid sample onto the culture medium. A turntable supports a culture medium container and the line is supported by a linearly movable slide. The position of the nozzle relative to the turntable is automatically adjusted in response to a signal from a sensor, which detects the level of the upper surface of the culture medium. An automatically controlled movement mechanism, together with a level control device or a disinfecting container, insures that the nozzle is submerged deep enough into the disinfectant to properly disinfect the outer side of the nozzle.

2 Claims, 5 Drawing Sheets

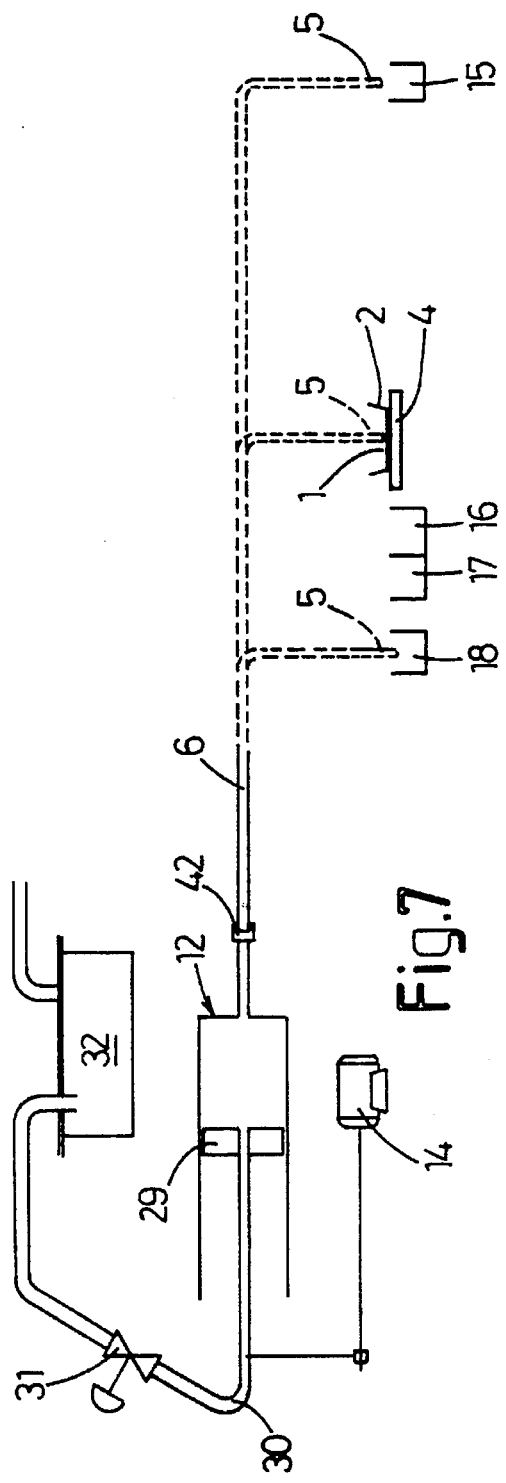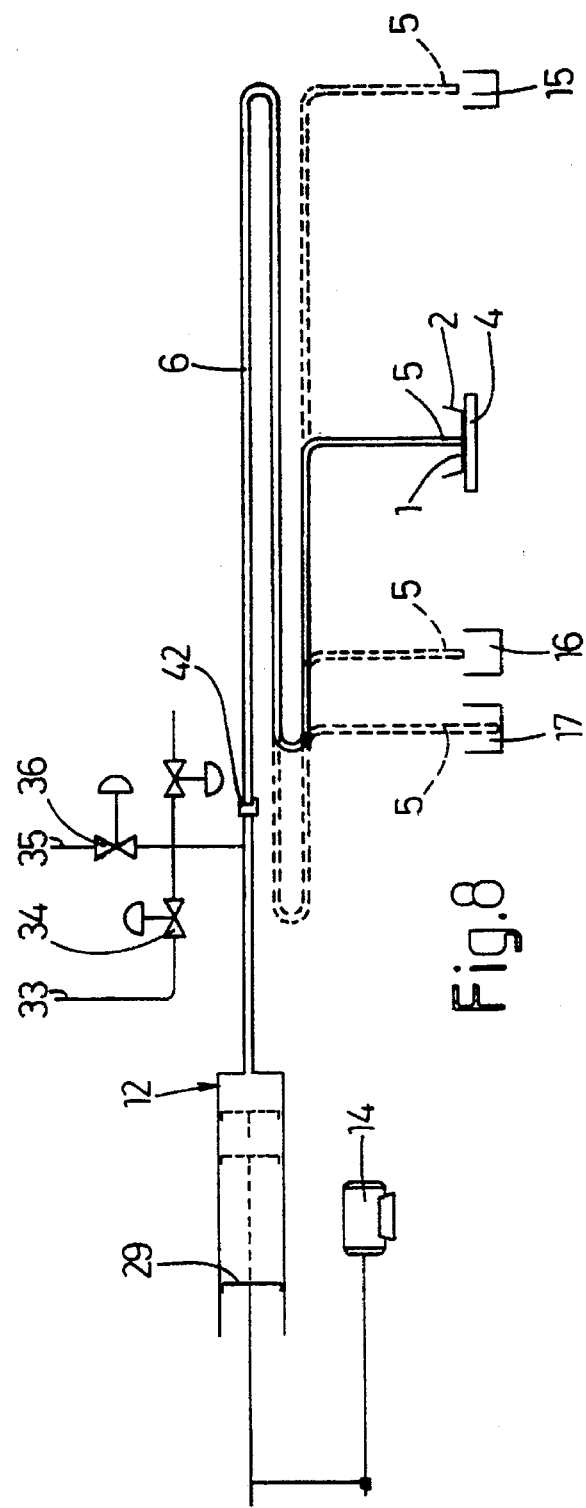

APPARATUS FOR APPLYING A LIQUID SAMPLE ONTO A CULTURE MEDIUM

BACKGROUND OF THE INVENTION

The present invention relates to an apparatus for applying a liquid sample onto a culture medium with a prescribed quantity and distribution, comprising a syringe, a movable nozzle connected to the syringe through a line, a table for a culture medium container, a container for sample liquid, a container for desinfectant, and a control system and movement mechanism for displacing the nozzle.

In a prior art apparatuses of this type, for example, U.S. Pat. Nos. 3,799,844; 3,892,632 and 3,962,040, the sample liquid is applied in a spiral shape onto a so-called agar culture medium. The agar culture medium is applied to the culture medium container, such as a Petri dish, as uniformly as possible and with a prescribed thickness. However, in practice this thickness varies several millimeters. As a result thereof the accurate angular positioning of the nozzle resting on the culture medium is complicated.

Furthermore, problems may arise in the prior art apparatus because the manual desinfection of the line and the nozzle are not carried out properly, which may cause cross-infections of samples.

SUMMARY OF THE INVENTION

The object of the invention is to provide an apparatus, in which the disadvantages as described are removed in an effective way.

According to a first aspect the apparatus according to the invention is characterized by means for automatically ensuring the nozzle of the line to be submerged deeper into the desinfectant than into the sample liquid by means of the movement mechanism.

In this way, a full cleaning operation of the nozzle is ensured and contamination of samples is prevented in a reliable way. In an advantageous embodiment and for this purpose said means comprises an automatic supply of desinfectant from a reservoir to the container thereof for maintaining a minimum level therein, and preferebly the nozzle is reciprocable up and down by means of a movement mechanism for moving it into and out of the desinfectant.

A further measurement for preventing samples in the apparatus to be infected or contaminated is that, in which the volume of the line and nozzle up to the syringe is larger than the volume of the sample liquid, which can maximally be applied. Due to this measure it is impossible for the sample liquid to arrive in the syringe itself when it is sucked in by means of the syringe, in which desinfection is more difficult than within the line. Consequently the risk of infections is substantially reduced in this manner.

According to a second aspect the invention provides an apparatus for applying a liquid sample onto a culture medium in a spiral shape, e.g. for determining the bacteria concentration therein, comprising a line having an inclined nozzle for applying the liquid sample onto the culture medium, a turntable for supporting a culture medium container, wherein the line is supported by a linearly movable slide, characterized by automatic means for adjusting the nozzle and the turntable relative to each other depending on the thickness of the culture medium by means of a sensor.

The invention will hereafter be elucidated with reference to the drawings very schematically showing the embodiments of the apparatus according to the invention by way of example.

BRIEF DESCRIPTION OF THE DRAWINGS

FIGS. 7 and 8 show diagrams of two embodiments of the liquid reception and delivery system according to the invention.

DETAILED DESCRIPTION OF THE PREFERRED EMBODIMENTS

Figure 2:
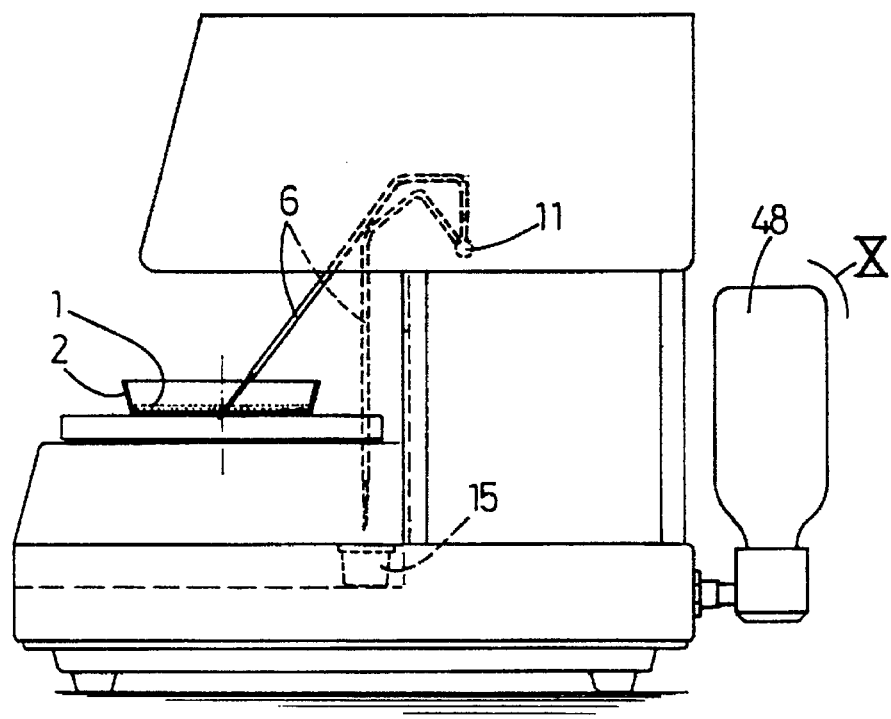
FIG. 2 is a side view of the apparatus of FIG. 1.

The drawings show an apparatus for applying a liquid sample onto a culture medium 1 in a prescribed quantity and distribution, for example for determining the bacteria concentration therein, for testing the sensitivity of bacterias to antibodies and for analysing mutagenicities. The culture medium 1 is here a layer of agar applied to the bottom of a Petri dish 2 serving as culture medium container.

In the present case, the sample liquid is applied to the culture medium 1 in the configuration of an Archimedes spiral, as is know per se. In this process the quantity of liquid per unit length of the spiral may be decreased continuously from the center so that the concentration of bacterias also decreases from the inside to the outside. It is for example possible when the spiral is applied to decrease the liquid delivery to the culture medium 1 in the Petri dish 2 in an exponential manner as a function of time so that very divergent bacteria concentrations may be counted on one culture medium also because the liquid concentration already decreases from the centre of the spiral due to the increasing surface speed of the culture medium with a greater radial distance from the centre. Another liquid distribution on the culture medium can be obtained with constant liquid delivery. The liquid quantity is then decreasing inversely proportional to the radial distance from the centre. On the other hand a uniform liquid distribution over the culture medium may be obtained if the liquid delivery is increased linearly to compensate the increasing surface speed of the culture medium in outward direction.

For effecting the spiral shape on the culture medium 1, the Petri dish 2 is rotated accurately by a turntable 4 driven by a motor 3, while a nozzle 5 at the end of a line 6, with which the liquid is delivered to the culture medium, is simultaneously moved linearly outwardly from the centre of the Petri dish 2. For this purpose, the end part of the line 6 is movably mounted to a slide 7 through a pivotable carrier 37, said slide being movable along a linear guide 8 and may be displaced by means of a screwed spindle 10 rotatably driven by a motor 9.

Figure 3:
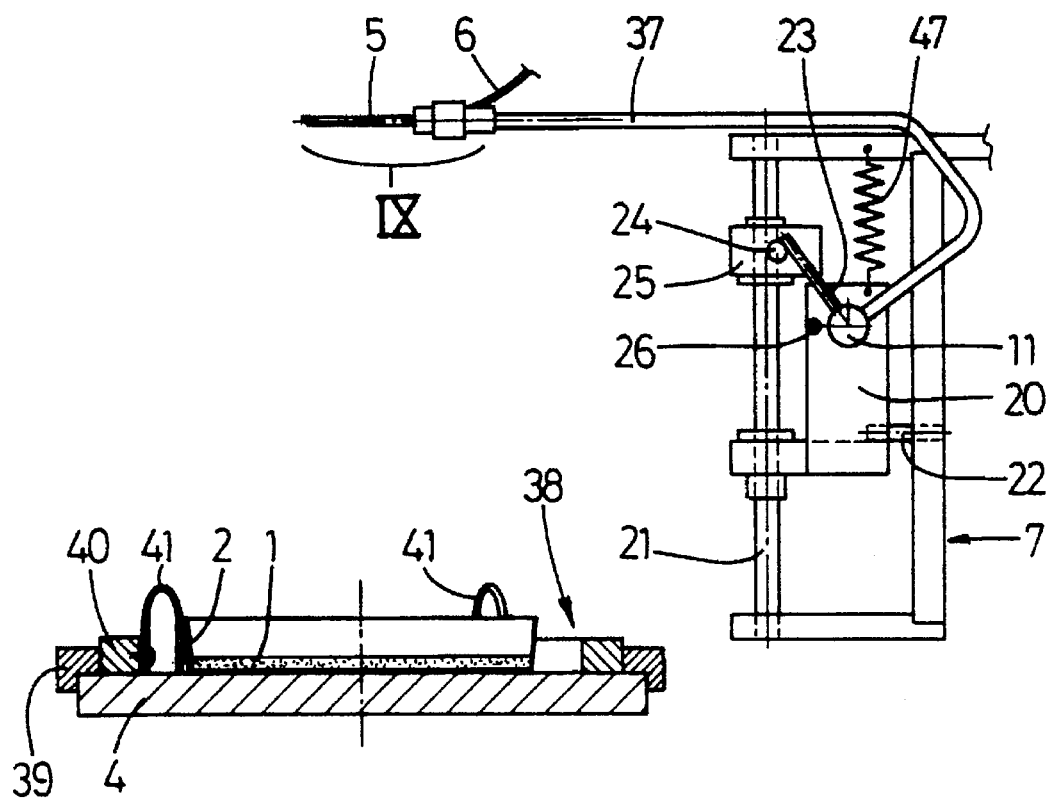
FIGS. 3–6 show on an enlarged scale a detached detail of the apparatus of FIGS. 1 and 2, in different positions.

As is shown by FIG. 3, the turntable 4 comprises an exchangeable centering device 38 for the Petri dish 2, with which both Petri dishes of different diameters and Petri dishes having diameter tolerances may be accurately positioned and held. Said diameter tolerances, which may for example vary between a few tenths of millimeters and several millimeters, occur between Petri dishes of different manufacturers. The centering device 28 consists of an outer ring 39 for clamp mounting to the turntable 4 and an exchangeable inner ring 40, to which three accurately similar spring means 41 equally distributed around the inner circumference of the inner ring are secured. This spring means consists of leaf springs bent substantially 180 degrees and of which one end being fixed to the inner ring 40 and the other end resting on the upper surface of the turntable 4 and being free to move in radial direction when a Petri dish 2 is urged between the springs 41 from above. Because the free end of the leaf spring 41 rests on the turntable 4 no downward movement of the free spring leg can occur when the Petri dish 2 is pushed in so that it also cannot spring back subsequently, which could cause that the Petri dish 2 does not stand planar on the turntable 4.

Figure 1:
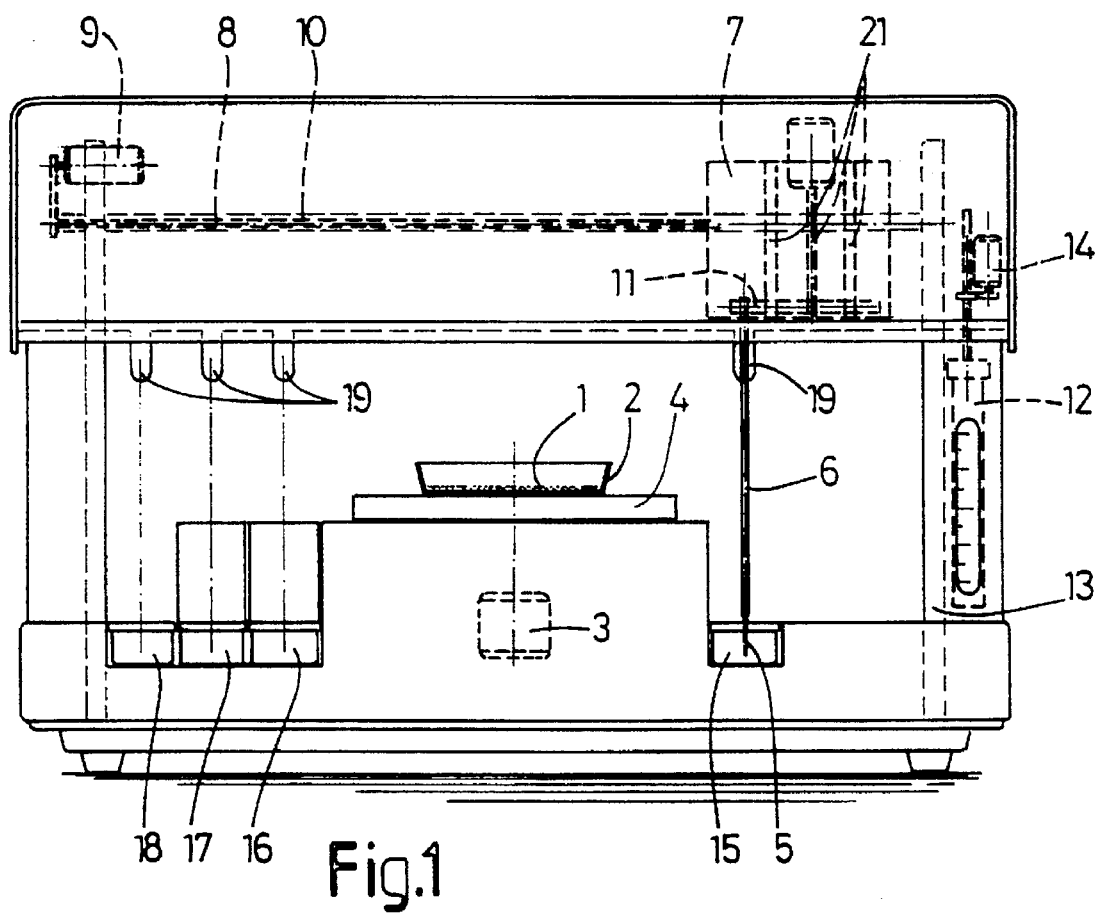
FIG. 1 is a schematic front view of the examplary embodiments of the apparatus according to the invention.

The carrier 37 is connected to the slide 7 pivotable about a shaft 11, and the line 6, which is not fully shown in FIGS. 1 and 2 and consists of a long flexible Teflon tube, is connected to a syringe 12, the cylinder of which is mounted stationarily to a frame 13 of the apparatus. The plunger of the syringe 12 is displaceable very accurately and in a programmable manner by means of a very schematically indicated step motor 14. To the various liquid flows and the operation of the apparatus will be referred later on.

Figure 9:
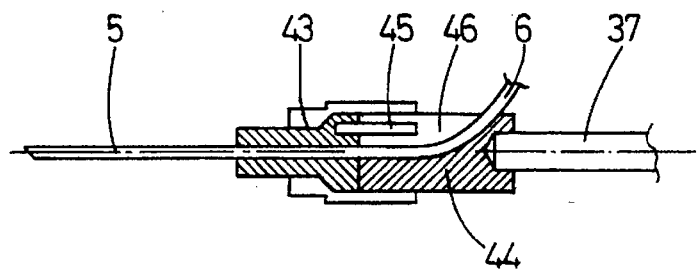
FIG. 9 shows on an enlarged scale and in cross section detail IX in FIG. 3.

FIG. 9 shows in detail in which manner the line 6 is releasably and exchangeably mounted to the carrier 37. The line 6, which is connected to the syringe 12 by a nipple 42 (FIG. 7), is equipped with a glued sleeve 43 at a required distance from the end thereof, said sleeve being adapted to be slid onto a holder 44 at the free end of the carrier 37. This is possible in only one way, that is when a projection 45 of the sleeve 43 fits into a recess 46 of the holder 44, through which also the line 6 is conducted to the outside. By this way of attachment of the line 6 an accurate length of the nozzle 5 is set, while the obliquely cut tip of the nozzle 5 is always properly positioned relative to the carrier 37. When the nozzle 5 is clogged, the whole line 6 can be exchanged in a very simple and quick manner rather than a front part of the line having to be cut in an exactly prescribed manner.

Particularly in FIG. 1 it is shown that the apparatus comprises a plurality of liquid containers, including a liquid container 15 for sample liquid, a liquid container 16 for waste liquid, a container 17 for desinfectant and a liquid container 18 for buffer liquid. Recesses 19 in the top of a house wall enable the nozzle 5 of the line 6 to be moved in a verticle position into and out of each liquid container 15–18.

Figure 4:
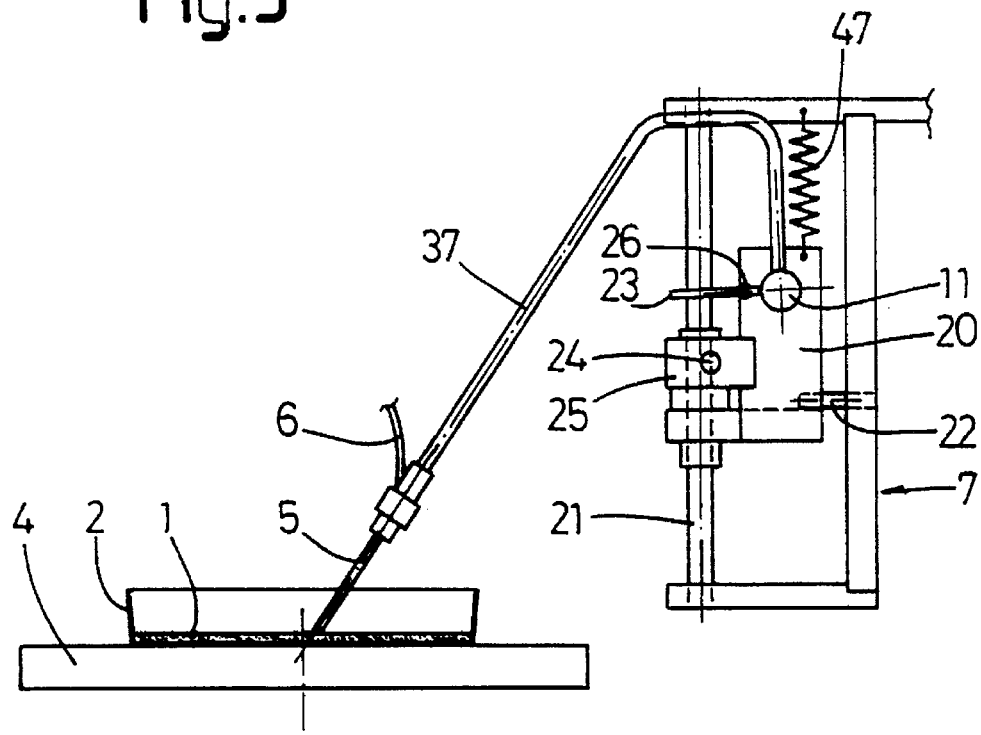
Figure 5:
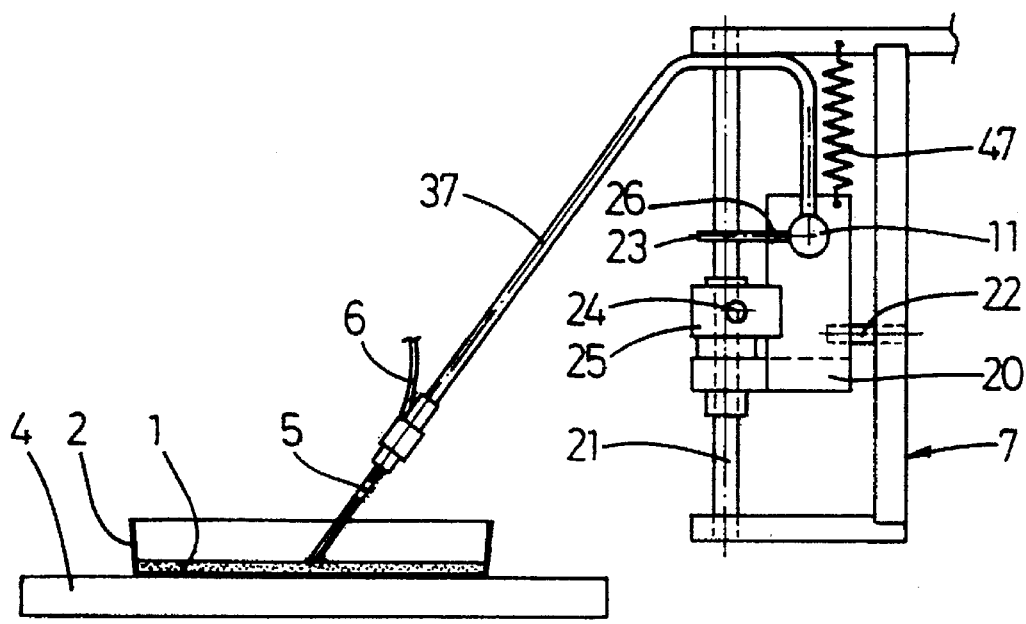

FIGS. 3–6 of the drawings show the various positions of the carrier 37 with the nozzle 5 of the line 6 during the operation of the apparatus, and FIGS. 3–5 illustrate especially the operation of the apparatus for the exact angular positioning of the nozzle 5 on the culture medium 1 of the Petri dish 2. For this purpose the rotary shaft 11, to which the carrier 37 is secured, is journalled in a bearing block 20. This block, which is adjustable in vertical direction is loaded upwardly by means of a tension spring 47 and in engagement with a stop 22 of the slide 7. An arm 23 is also mounted on the rotary shaft 11, with which a pin 24 may engage for pivoting the carrier 37 about the rotary shaft 11 and for displacing the block 20 downwardly, said pin 24 being part of a carriage 25, which is displaceable in vertical direction by a further combined spindle drive and linear guide 21. The arm 23 further co-operates with a sensor 26, such as a proximity switch, to determine the horizontal position of the arm 23. The operation of the movement mechanism for the carrier 37 and the nozzle 5 of the line 6 is as follows.

In FIG. 3, the nozzle 5 is shown in its inoperative horizontal position, in which it is transported by the slide 7. Then the arm 23 rests on the pin 24 of the carriage 25, which is in its highest position. Also the block 20 is in its highest position.

In FIG. 4, the carriage 25 is displaced so far downwardly that the nozzle 5 is pivoted by the carrier 37 about the rotary shaft 11 to such an extent that the nozzle 5 has come to rest on the culture medium 1 and the pin 24 of the carriage 25 has released from the arm 23. As is clearly shown in FIG. 4, the tip of the nozzle 5 is not in the centre of the culture medium 1 and consequently not in the centre of the turntable 4 because the culture medium 1 is thinner than nominal and as a result the nozzle 5 is pivoted too far about the rotary shaft 11. In this position of the nozzle 5 it is not possible to apply a prescribed spiral of sample liquid on the culture medium 1, and the obliquely cut tip of the nozzle 5 is also not parallel to the surface of the culture medium 1, which prevents the formation of a proper liquid cushion between the culture medium 1 and the nozzle 5 when the spiral is applied.

The wrong angular position of the nozzle 5 is sensed by the sensor 26 registrating that the arm 23 of the rotary shaft 11 is not horizontal. This is transmitted to the control means activating the spindle drive 21 of the carriage 25 on basis of this information in order to displace the block 20 slightly downwardly against the spring force of the tension spring 47 lowering the rotary shaft 11 of the nozzle 5 and thereby correcting the angle of the nozzle 5.

In FIG. 5 it is shown that the block 20 together with the rotary shaft 11 is displaced downwardly to such an extent that the arm 23 is now horizontal and the nozzle 5 is positioned at the right angle, in this case 54°, automatically positioning the tip of the nozzle 5 in the centre of the turntable 4. In this position of the nozzle the application of the sample liquid on the culture medium 1 in a spiral shape may be commenced.

Figure 6:
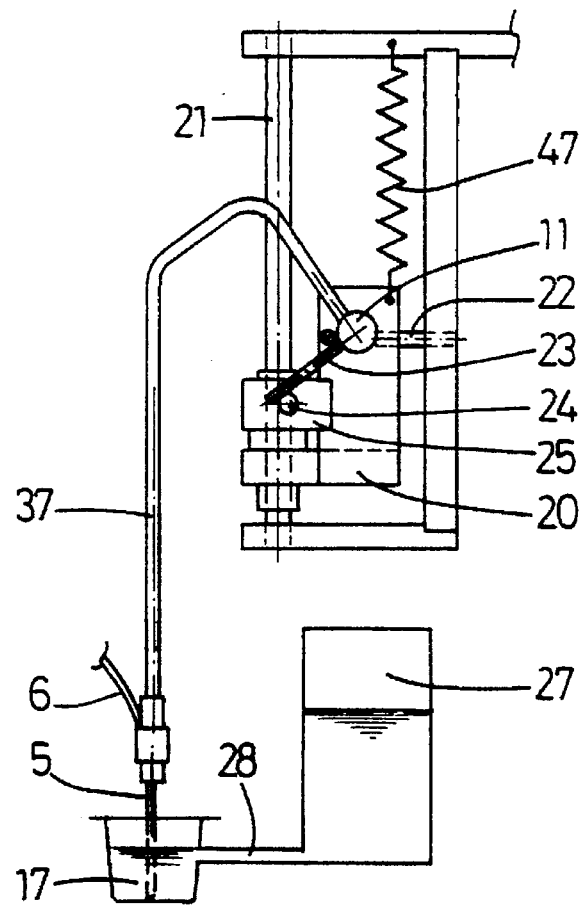

FIG. 6 shows the position of the carrier 37 with the nozzle 5 of the line 6, in which the nozzle is submerged in the liquid of a liquid container, in this case in desinfectant of the liquid container 17. In this position, the block 20 and the carriage 25 are moved maximum downwardly such that the nozzle 5 is pivoted to a vertical position. The nozzle is also moved downwardly into the liquid container 17. When the nozzle 5 is desinfected it is of great importance that the outer side of the nozzle is desinfected over a length, which is greater than the length of the portion of the nozzle 5, which has been submerged in the sample liquid. Only then a complete desinfection takes place. In order to ensure this, the liquid level is maintained at a sufficiently high level, in this case by means of the reservoir 27 as shown. This reservoir 27, which is fully closed and is connected to the liquid container 17 only through a connection line 28, contains a sufficient supply of desinfectant. Because there is an underpressure above the liquid in the reservoir 27, no liquid is able to flow from the reservoir through the connection line 28 to the liquid container 17. Only when the level of the liquid in the liquid container 17 drops under the connection line 28, air is permitted to pass into the reservoir and hence liquid may flow from the reservoir 27 to the liquid container 17 until the level thereof is so high that the connection line 28 is sealed to air. In this manner, the liquid level in the liquid container 17 is maintained just above the connection line 28.

Figure 10:
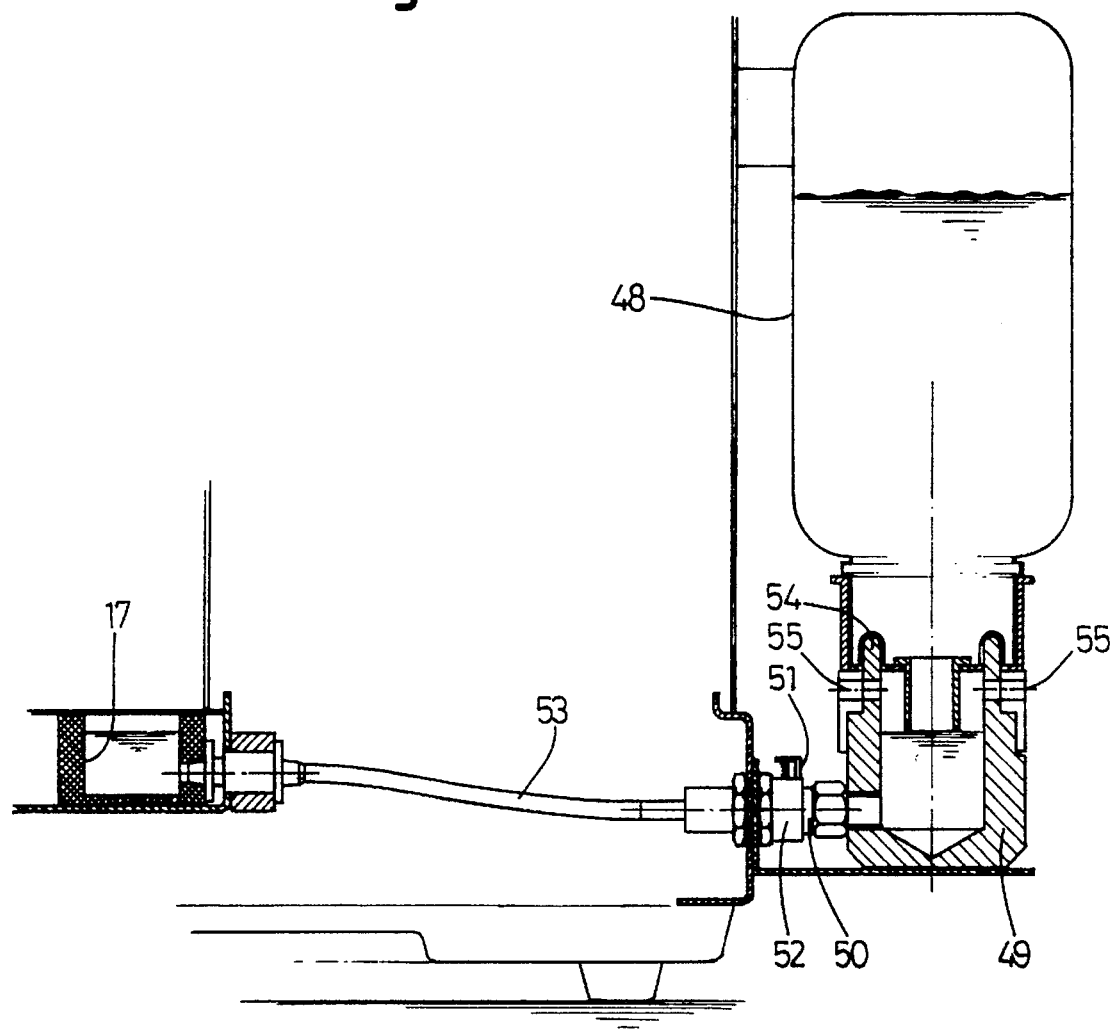
FIG. 10 shows on an enlarged scale and in cross section detail X in FIG. 2.

FIG. 10 shows another development of the level device of FIG. 6, in which the reservoir consists of a bottle 48, which is connectable in an upside down position through a special cap 49 having a nipple 50 to a connection 52 having an automatically closing valve 51. The connection 52 communicates through a tube 53 with the desinfectant container 17. Between the bottle 48 and the cap 49 is a passage spout 54, of which the lower end is at a level equal to the desired level in the liquid container 17. Then, when the liquid in the cap 49 extends up to the lower edge of the passage spout 54 no liquid can flow out of the bottle 48, due to an underpressure above the liquid therein. Only when the liquid level in the liquid container 17 drops, also the level in the cap 49 drops and when it arrives below the lower edge of the passage spout 54, air may pass into the bottle 48 through holes 55 in the cap 49 enabling liquid to escape therefrom until the liquid closes the passage spout 54 again. This level device operates quickly and accurately, and the exchange of bottle 48 and cap 49 can be carried out quickly and without causing a mess thanks to the connection 52 having an automatically closing valve 51.

FIGS. 7 and 8 show a diagram of two embodiments of the syringe 12 and parts connected therewith. In the embodiment of FIG. 7, the plunger 29 of the syringe 12 is hollow and a space in front of the plunger 29 can be connected through a line 30 having a valve 31 to a vacuum source 33 for sucking in liquid through the nozzle 5.

With reference to particularly FIG. 7 the operation of the apparatus according to FIG. 1–7 is explained.

In the initial position of the apparatus, in which the nozzle 5 of the line 6 is in its right hand position above the sample liquid container 15, the whole line 6 and the nozzle 5 are filled with buffer liquid, such as distilled water. The nozzle 5 is then moved downwardly into the sample liquid container 15 and then the plunger 29, which is in the front position, is moved back by means of the step motor 14 thereby sucking sample liquid into the line 6. The valve 31 is closed of course. The nozzle 5 is then moved up and displaced horizontally to a position above the turntable 4 where the nozzle 5 is put down onto the culture medium 1 in the Petri dish 2. By means of the height adjustment described with reference to FIGS. 3–5, the nozzle 5 is adjusted into the correct angular position to the culture medium 1. Then the turntable 4 is rotated and simultaneously the nozzle 5 is moved horizontally and radially outwardly, while sample liquid is applied to the culture medium 1 in a controlled quantity as a result of a very accurate displacement of the plunger 29 by the step motor 14. After completing the application of the liquid sample on the culture medium 1, the nozzle 5 is raised and is brought to a position above the liquid container 16 for waste liquid and the line is drained from any residual sample liquid by means of the plunger 29. The nozzle 5 is then submerged deeply into the desinfectant, such as chlorine or alcohol, in the liquid container 17 and the valve 31 is opened so that the liquid is sucked in through the line 30 by means of the vacuum source 32. Then the nozzle 5 is brought to the buffer liquid container 18 and this buffer liquid is sucked in by opening again the closed valve 31. Simultaneously the plunger 29 is moved back to the initial position in order to be able to suck in a next sample by reverse displacement of the plunger 29. Then the cycle is completed. On the other hand, it is also possible to apply a sample to several Petri dishes (e.g. with different quantities) or to suck in a new quantity of a similar sample from the sample liquid container without cleaning operation.

It is noted that the volume of the nozzle 5 and the line 5 is such that it is larger than the maximum volume of a liquid sample, or the maximum stroke volume of the syringe 12, respectively. A normal volume of a liquid sample is approximately 80 cubic millimeters and the syringe 12 and the line 6 have a volume of preferably approximately 250 cubic millimeters. With a line diameter of 0.5 millimeters, a length of the line 6 of approximately 1.5 meters is selected. Due to these dimensions it is not possible that sample liquid arrives in the syringe 12 where a desinfection would be more complicated. When the sample liquid is only present within the line 6, simply flushing the line with desinfectant is sufficient for a complete desinfection.

The alternative embodiment of FIG. 8 differs from that of FIG. 7 in that no liquid container for buffer liquid is present and lines including valves are connected to the line 6 in front of the syringe 12 in order to supply buffer liquid and desinfectant. In this way it is possible to connect a line 33 containing a valve 34 to a reservoir for desinfectant (not shown) while a line 35 including a valve 36 communicates with a reservoir for buffer liquid. When in this embodiment a sample has been applied to the culture medium, the nozzle 5 is brought above the waste liquid container 16 and the valve 34 of the desinfectant line 33 is opened so that the line 6 is flushed by desinfectant. The nozzle 5 is then submerged in the desinfectant in the desinfectant container 17 in order to desinfect the outer side thereof. After desinfection of the line 6 and the nozzle 5 by desinfectant, the valve 36 in the line 35 for buffer liquid is opened so that the whole line 6 and the nozzle 5 are filled with buffer liquid. The nozzle 5 is then submerged in the sample liquid container 15 and by moving the plunger 29 back the sample liquid is sucked in whereafter the application of sample liquid can be repeated in the way described hereinbefore.

The invention is not restricted to the embodiments shown in the drawings and described hereinbefore, which can be varied in different manners within the scope of the invention. The apparatus may for example be equipped with automatically controlled means for exchanging the Petri dishes and the sample liquid containers. In this manner it is possible to apply a great number of samples onto culture mediums without human interference.

What is claimed:

1. An apparatus for applying a liquid sample onto a culture medium with a prescribed quantity and distribution, the apparatus comprising a syringe and a line connected thereto and having at one end a nozzle with an oblique cut tip for delivering sample liquid and at its other end being exchangeably connected to the syringe with a nipple, wherein for positioning said nozzle the line is connected to a movable carrier with a mounting means for unambiguously and exchangeably mounting the nozzle in a fixed position relative to a holder of the carrier.

2. A line for use in an apparatus for applying a liquid sample onto a culture medium with a prescribed quantity and distribution, which line is connectable to a syringe and comprises at one end a nozzle with an oblique cut tip for delivering sample liquid and at its other end being exchangeably connectable to the syringe with a nipple, wherein for positioning said nozzle the line has mounting means for unambiguously and exchangeably mounting the nozzle in a fixed position relative to a holder of a carrier.

* * * * *